United States Patent
Ledvina et al.

(10) Patent No.: US 11,492,327 B2
(45) Date of Patent: Nov. 8, 2022

(54) AMINOOXYLIPIDS FOR THE CONSTRUCTION OF SELF-ASSEMBLING LIPOSOMAL SYSTEMS ENABLING THEIR SUBSEQUENT MODIFICATION BY BIOLOGICALLY FUNCTIONAL MOLECULES

(71) Applicants: VYSOKA SKOLA CHEMICKO-TECHNOLOGICKA V PRAZE, Prague (CZ); VYZKUMNY USTAV VETERINARNIHO LEKARSTVI, V. V. I., Brno (CZ); APIGENEX S.R.O., Prague (CZ)

(72) Inventors: Miroslav Ledvina, Prague (CZ); Roman Effenberg, Celakovice (CZ); Jaroslav Turanek, Brno (CZ); Elissa Bartheldyova, Unin (CZ); Ladislav Droz, Prague (CZ); Josef Masek, Brno (CZ); Frantisek Hubatka, Brno (CZ)

(73) Assignees: VYSOKA SKOLA CHEMICKO-TECHNOLOGICKA V PRAZE, Prague (CZ); VYZKUMNY USTAV VETERINARNIHO LEKARSTVI, V. V. I., Brno (CZ); APIGENEX S.R.O., Prague (CZ)

( * ) Notice: Subject to any disclaimer, the term of this patent is extended or adjusted under 35 U.S.C. 154(b) by 791 days.

(21) Appl. No.: 16/336,844

(22) PCT Filed: Nov. 2, 2017

(86) PCT No.: PCT/CZ2017/050054
§ 371 (c)(1),
(2) Date: Mar. 26, 2019

(87) PCT Pub. No.: WO2018/082723
PCT Pub. Date: May 11, 2018

(65) Prior Publication Data
US 2021/0292275 A1    Sep. 23, 2021

(30) Foreign Application Priority Data
Nov. 3, 2016 (CZ) .............................. CZ2016-685

(51) Int. Cl.
C07C 239/20     (2006.01)
A61K 47/69      (2017.01)
A61K 47/61      (2017.01)
A61K 47/54      (2017.01)
A61K 47/68      (2017.01)
A61K 9/127      (2006.01)

(52) U.S. Cl.
CPC .......... *C07C 239/20* (2013.01); *A61K 9/1271* (2013.01); *A61K 47/543* (2017.08); *A61K 47/61* (2017.08); *A61K 47/6835* (2017.08); *A61K 47/6913* (2017.08)

(58) Field of Classification Search
None
See application file for complete search history.

(56) References Cited

U.S. PATENT DOCUMENTS 9,393,200 B2    7/2016   Drasar et al.
2005/0287202 A1  12/2005  Miller

FOREIGN PATENT DOCUMENTS

CZ           303963 B6    7/2013

OTHER PUBLICATIONS

Kenichi Niikura et al: "Versatile Glycoblotting Nanoparticles for High-Throughput Protein Glycomics", Chemistry—A European Journal, vol. 11, No. 13, Jun. 20, 2005 (Jun. 20, 2005), pp. 3825-3834, XP055457715, DE ISSN: 0947-6539, abstract.
International Search Report and Written Opinion for corresponding PCT application No. PCT/CZ2017/050054, dated Mar. 16, 2018.

*Primary Examiner* — Sudhakar Katakam
*Assistant Examiner* — Jennifer C Sawyer
(74) *Attorney, Agent, or Firm* — Notaro, Michalos & Zaccaria P.C.

(57) ABSTRACT

New aminooxylipids of general formula I, wherein $n_1$=5-30 and X is polymethylene linker of the general formula II where $n_2$=2-10, or X is polyethylene glycol linker of the general formula III, wherein $n_3$=1-14 are provided. A method of preparation of the aminooxylipids of general formula I characterized in that the acylation of N-tert-butoxycarbonyl-polymethylenediamine $\{(CH_3)_3C-O-(C=O)-HN-(CH_2)_n-NH_2$, n=2-13$\}$, or N-tert-butoxycarbonyl-polyethyleglycoldiamine $\{(CH_3)_3C-O-(C=O)-HN-(CH_2)_2-[O-(CH_2)]_n-O-(CH_2)_2NH_2$, n=1-14$\}$ with in position C(2) symmetrically branched fatty acids of general formula IV, wherein $n_1$=5-30, in the presence of condensation reagent, or from acid of general formula IV derived acylchloride of general formula V wherein $n_1$=5-30, produces N-Boc-aminolipids of general formula VI, wherein $n_1$=5-30 a X is polymethylene linker of the general formula II or X is polyethylene glycol linker of the general formula III.

2 Claims, 6 Drawing Sheets

Fig. 11

# AMINOOXYLIPIDS FOR THE CONSTRUCTION OF SELF-ASSEMBLING LIPOSOMAL SYSTEMS ENABLING THEIR SUBSEQUENT MODIFICATION BY BIOLOGICALLY FUNCTIONAL MOLECULES

FIELD OF ART

The present invention provides novel amino group-containing lipids with suppressed cytotoxicity, a method of their preparation and their use for the construction of self-assembling liposomal drug carriers presenting aminooxy groups. These lipids can be "post-liposomally" covalently modified by biologically functional molecules bearing aldehyde or ketone groups using oxime ligation technique (binding counterparts: an aminooxy group and an aldehyde or ketone group).

BACKGROUND ART

Self-assembling nanostructured liposomal systems, due to their biocompatibility, biodegradability, low toxicity and the ability to internalize substances of different physicochemical properties, are currently one of the most in-depth studied platforms for targeted drug delivery in vivo that have already found a number of clinical applications. For the internalization of biologically functional substances, both their internal space and their envelope composed of a phospholipid bilayer can be used. Hydrophilic substances/therapeutics can be encapsulated into the internal aqueous space, and the phospholipid bilayer allows anchoring of biomolecules through their hydrophobic domain (Koudelka, Š. et al. 2016). The latter principle was used in the construction of vector biomolecules of targeted liposomes and liposomal vaccines (Marques-Gallego, P. et al. 2014; Turánek, J. et al. 2012). During the introduction of vector molecules into the lipid bilayer, two basic methods are employed: The first is based on their application through a vector molecule of a modified lipid as a co-lipid during liposome construction. The second method is based on the "post-liposomal modification" of pre-formed liposomes. The co-lipid, used in the second method, is a lipid presenting a structural motif that allows the vector molecule to be anchored into the surface of the pre-formed liposome. The conventional post-modification methods for liposomes are based on reactions such as formation of amide bonds and disulphide bridges, interconnection of amines through a homobifunctional cross-linker and the addition of thiol across the double C=C bond of maleinimide. These methods share a common disadvantage, which is a low orthogonality (chemoselectivity) of the above mentioned reactions in relation to the other functional groups present in the complex biomolecule to be ligated (bound). Therefore, in recent years, the attention has been paid to the development of bioorthogonal ligation methods based on a chemoselective reaction between two functional groups. None of these groups is present in the native biomolecule, which eliminates the formation of byproducts. Another criterion for these reactions is that they should proceed under mild reaction conditions in an aqueous medium, with a high conversion and at a sufficient rate. The term "click-chemistry" was introduced for the ligation techniques meeting these requirements. A typical representative of "click" techniques is a ligation based on the monovalent copper-catalyzed Huisgen 1,3-dipolar cycloaddition of an azide to give a triple bond (Hassane, F. S. et al., 2006). Problems with the use of copper salts in biological systems have further been solved by the development of "Copper-Free Click Chemistry" where the azide cycloaddition to fluorine-activated triple bond in the 2,2-difluoro cyclooctyne ring occurs (Baskin, J. M. et al. 2007). Likewise, Staudinger ligation does not require catalysis. This ligation is based on Staudinger reduction of organic azides to amines through the action of triphenylphosphine. In the case of Staudinger ligation, the binding co-lipid presents a triphenylphosphine structural motif bearing, at the same time, a methoxycarbonyl group at the ortho-position, which allows subsequent binding of a reduction-formed amine via an amide bond (Vabbilisetty, P. et al. 2014).

Oxime ligation, based on spontaneous condensation of an amino group with an aldehyde group or ketone group, is also included in the category of bioorthogonal "click" ligations (Ulrich, S. et al. 2014). Oxime ligation is an alternative to reductive amination which does not require catalysis. The resulting oxime with $K_D=10^{-8}M$ is considerably more resistant to hydrolysis than imines. Oxime ligation takes place under conditions favourable for biological systems and is orthogonal to most functional groups present in biomolecules, including amino groups, making it an ideal ligation technique for postliposomal modifications. In the case of post-liposomal ligations, the following are described as cationic aminooxy groups presenting colipids: single-stranded aminooxylipids with a hydrophobic domain consisting of a linear hydrocarbon chain (Tang, L. 2015), and double-stranded amiaminooxylipids with a hydrophobic domain based on symmetrical lipophilic di-O-acyl- or di-O-alkyl derivatives of glycerol and symmetrical secondary amino acid dialkyl amides (Liu, Y. et al. 2007; Miller, A. D. et al. 2005). A specific group is represented by aminooxy lipids whose hydrophobic domain is composed of planar polycyclic cholesterol attached to the cationic domain through a urethane linker (Miller, A. D. a spol. 2005; Carmona, S. et al. 2009).

The overall geometry of the hydrophobic domain of the cationic aminooxylipids has a fundamental influence on the formation of structural phases in solutions and on the stability of the lipid bilayer. Double-stranded cationic lipids are more similar in structure to the double-stranded hydrophobic domain of phospholipids, and in an aqueous solution they self-assemble into spherical liposomes, thereby more easily producing lipid bilayers as compared to single-stranded lipids. On the other hand, single-stranded cationic lipids have an increased tendency to form micelles or reverse micelles (Niculescu-Duvaz, D. et al. 2003; Tsukamoto, M. et al. 1995). The hydrophobic character of the domain can also influence its toxicity. Cationic lipids whose hydrophobic domain is constituted by lipophilic acyl residues are generally less toxic due to their biodegradability, compared with cationic lipids with a hydrophobic domain based on lipophilic alkyl chains (Leventis, R. et al. 1990; Lv, H. et al. 2006). Taking into consideration the above mentioned facts, the double-stranded lipophilic domain based on synthetically easily available fatty acids symmetrically branched in position C(2) appears to be very attractive. This domain has been successfully applied in the design of novel polycationic lipids as composites for the construction of polycationic liposome transfection systems (Korvasova, Z. et al. 2012; Drašar, L. et al. 2013: Czech. Pat. A PCT appl., Drašar, L. et al. 2016 U.S. Pat. No. 9,393,200 B2). If there is an even number of carbon atoms in their alkyl chains, these acids are degradable in the body by β-oxidation as are the biogenic fatty acids with an even number of carbon atoms.

DISCLOSURE OF THE INVENTION

By using synthetically easily available fatty acids symmetrically branched in position C(2), resistant to solvolytic degradation, as a hydrophobic domain in aminooxylipids, the invention solves the following problems: (a) difficulties in the synthesis of cationic aminooxylipids containing two symmetrical aliphatic hydrophobic domains based on symmetrical lipophilic diacyl derivatives and dialkyl derivatives of glycerol as well as on symmetrical secondary amino acid dialkylamides; (b) a limited stability of diacylderivatives of glycerol and the urethane linker in lipopolyamines derived from cholesterol; (c) a problem of degradation of aminooxylipids whose hydrophobic domain is formed by linear 0- and N-alkyl chains.

The subject-matter of the invention are aminooxylipids of general formula I wherein $n_1$=5-30 and X is a polymethylene linker of general formula II wherein $n_2$=2-10
or a polyethyleneglycol linker of general formula III wherein $n_3$=1-14.

Another object of the invention is that aminooxylipids of the general formula I preferably have $n_1$=13 and linker X of the above-mentioned general formula II wherein $n_2$=2 or $n_2$=3.

The invention is also characterized by the fact that aminooxylipids of general formula I preferably have $n_1$=13 and linker X of the aforementioned general formula III, wherein $n_3$=1.

An object of the invention is also a method for preparation of aminooxylipids of general formula I. Fatty acids symmetrically branched in position C(2) of general formula IV wherein $n_1$=5-30 (available using a method published by Kusumoto, S. et al. 1978) are transformed by means of a reaction with oxalyl chloride in the presence of a catalytic amount of N,N-dimethylformamide in an organic aprotic solvent (preferably in dichloromethane), to their acyl chlorides of general formula V wherein $n_1$=5-30.

The condensation of said acyl chlorides of general formula V with commercially available N-tert-butoxycarbonyl-polymethylenediamines {$(CH_3)_3C$—O—(C=O)—HN—$(CH_2)_n$—$NH_2$, n=2-13}, or N-tert-butoxycarbonyl-polyethyleneglycoldiamines {$(CH_3)_3C$—O—(C=O)—HN—$(CH_2)_2$—[O—$(CH_2)$]$_n$—O—$(CH_2)_2NH_2$, n=1-14} in an organic aprotic solvent and in the presence of an organic base (preferably in the presence of N,N-diisopropylethylamine in dichloromethane) yields aminolipids of general formula VI wherein $n_1$=5-30 and X is the polymethylene linker of the above general formula II or the polyethyleneglycol linker of the above general formula III.

Hydrolytic cleavage of the N-tert-butoxycarbonyl protecting group (known as debocylation) from the compounds of general formula VI (preferably using trifluoroacetic acid in dichloromethane) yields aminolipids of formula VII wherein $n_1$=5-30 and X is the polymethylene linker of the above general formula II or the polyethyleneglycol linker of the above general formula III.

N,N"-Diisopropylcarbodiimide-promoted condensation of N-tert-butoxycarbonylaminooxyacetic acid with aminolipids of general formula VII yields N-Boc-aminooxylipids of general formula VIII

VIII wherein $n_1$=5-30 and X is the polymethylene linker of the above formula II or the polyethyleneglycol linker of the above mentioned general formula III.

By hydrolytic cleavage of the N-tert-butoxycarbonyl protecting group of the compounds of general formula VIII (preferably using trifluoroacetic acid in dichloromethane), the target aminooxylipids of general formula I are obtained.

Another object of the present invention is the use of aminooxylipids of general formula I for the construction of non-toxic self-assembling liposomal drug carriers presenting aminooxy groups and their "post-liposomal" modification by biologically functional molecules using oxime ligation (binding pairs: an aminooxy group and an aldehyde or ketone group).

The fact that incorporation of aminooxylipids of general formula I into the liposomal bilayer of liposomes does not result in an increase in its cytotoxicity was demonstrated by comparing the cytotoxicity of EPS liposomes and EPS liposomes with incorporated aminooxylipid of general formula I in in vitro experiments using T-lymphocytes and H1299 cells of lung cancer cell line.

The ability of self-assembled liposomal drug carriers modified by aminooxylipids of general formula I to covalently bind biologically functional molecules carrying aldehyde or ketone groups has been demonstrated by binding of:
a) hyaluronic acid (8-15 kDa) via the reducing end of its molecule;
b) reductive amination of fluorescein-labelled hyaluronic acid (50-200 kDa) modified to a limited extent at C-6 position of the N-acetylglucosamine subunit by aldehyde groups generated by controlled oxidation of primary OH groups;
c) mannan;
d) aldehyde functional groups of a modified protein, i.e. immunoglobulin IgY isolated from egg yolk, modified by aldehyde groups, generated by oxidative cleavage of its carbohydrate moiety.

Figure 11:
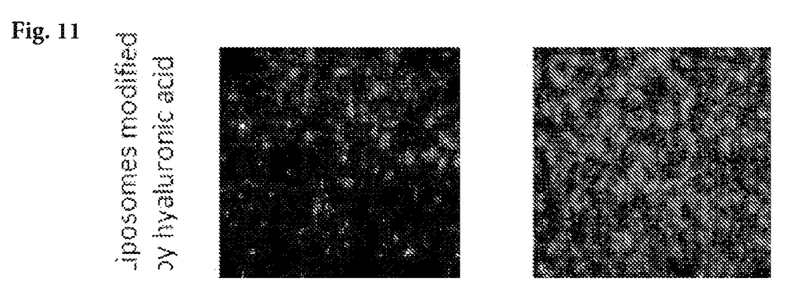
FIG. 11: Schematic representation of binding of molecules of the polysaccharide type (mannan, hyaluronic acid) to aminooxylipid-modified liposomes.

The binding of polysaccharide-type molecules (mannan, hyaluronic acid) to liposome-modified aminooxy lipids is strictly chemoselective and regioselective, i.e. via the reducing end of the polysaccharide, which results in uniform molecular orientation on liposomal surface (see FIG. 11). Random binding by crosslinkers (e.g., carbodiimide) cannot lead to defined chemoselective and regioselective binding.

BRIEF DESCRIPTION OF DRAWINGS

FIG. 4(a)-(d): TEM of liposomes with 1% aminooxylipid of general formula I (according to Example 14) (a) and IgY-bound liposomes (b): arrows indicate liposome surface-bound IgY molecules. The shape and orientation of IgY molecules is also visible (insert).

EXAMPLES OF CARRYING-OUT THE INVENTION

List of Abbreviations

NMR Nuclear magnetic resonance
ESI-MS Electrospray ionization mass spectrometry
FAB-MS Fast atom bombardment mass spectrometry
HR-MS High-resolution mass spectrometry
HA Hyaluronic acid
EPC Egg phosphatidyl choline (see EPC liposomes)
Cells H1299 Lung tumor cell line H1299
TEM Transmission electron microscopy
SEM Scanning electron microscopy
DLS Dynamic light scattering
PBS 20 mM phosphate buffered saline 0.14M NaCl, pH 7.2
DOPE 1,2-dioleoyl-sn-glycero-3-phosphoethanolamine Example 1

To a stirred suspension of 2-tetradecylhexadecanoyc acid (general formula IV; where $n_1$=13; 1.5 g, 3.32 mmol) in dichloromethane (50 ml), oxalyl chloride (0.42 g; 6.63 mmol) and catalytic amount of N,N-dimethylformamide were added. The reaction mixture was stirred at room temperature for 1.5 h. The solvent was distilled off, the residue was dissolved in benzene (100 ml) and the solution was washed with $H_2O$ (2×50 ml) and with saturated solution of $NaHCO_3$ (2×50 ml). The organic layer was dried over anhydrous MgSO$_4$ and concentrated in vacuo to afford 1.52 g (97%) of analytical pure 2-tetradecylhexadecanoylchloride V (where $n_1$=13). For C$_{30}$H$_{59}$ClO (471.24) calculated: 76.46% C, 12.62% H, 7.52% Cl. found: 76.28% C, 12.60% H, 7.32% Cl.

Example 2

To a stirred solution of 2-tetradecylhexadecanoylchloride (general formula V; where $n_1$=13; 0.39 g; 0.82 mmol) in dichloromethane (25 ml), N-tert-butoxycarbonyl-1,2-diaminoethane-hydrochloride ((CH$_3$)$_3$C—O—(C=O)—HN—(CH$_2$)$_n$—NH$_2$.HCL, n=2; 174 mg, 0.88 mmol) and subsequently N,N-diisopropylethylamine (240 µl) were added and the mixture was stirred at room temperature overnight. Then the mixture was diluted with dichloromethane (50 ml) and the obtained solution was washed with aq. NaHSO$_4$ (5%; 2×15 ml) and H$_2$O (2×15 ml). The organic layer was dried over anhydrous MgSO$_4$ and concentrated in vacuo. The crude products were purified by flash chromatography on silica gel column (110 ml) in toluene-ethyl acetate (gradient 0-63% ethyl acetate, 14 ml/min, 64 min, sample was applied to the column in chloroform). Homogenous fractions of the product was evaporated in vacuo and lyophilized from dioxane to give 445 mg (95% yield) of N$^1$-(2-tetradecylhexadecanoyl)-N$^2$-tert-butoxycarbonyl-1,2-diaminoethane (general formula VI; where $n_1$=13 and X=polymethylene linker of the general formula II, where $n_2$=2). IR (CHCl$_3$): ν=3347 (NH), 3308 (NH), 2919, 2850, 1689 (C=O; Boc), 1645 (Amide I), 1549 (Amide II), 1535 (Amide II), 1467, 1447, 1390 (CH$_3$; Boc), 1367 (CH$_3$; Boc), 1286, 1268, 1252, 1236, 1178, 938, 864, 719 cm$^{-1}$; $^1$H NMR (400 MHz, CDCl$_3$): δ=6.20 (s, N$^2$H); 4.96 (s, N$^1$H); 3.36 (dt, J=4.7, 4.7 Hz, 2H, H-1); 3.27 (dt, J=4.7, 4.7 Hz, 2H, H-2); 1.99 (spt, J=4.7 Hz, H-2'); 1.6-1.51 (m, 2H, H-3', H-1"); 1.43 (s, 9H, 3×CH$_3$); 1.41-1.36 (m, 2H, H-3', H-1"); 1.30-1.20 (m, 48H, 24×CH$_2$); 0.87 (t, J=7.0 Hz, 6H, H-16', H-14"); $^{13}$C NMR (100 MHz, CDCl$_3$): δ=176.94 (C-1'), 156.87 (N$^2$C), 79.65 (C(CH$_3$)$_3$), 48.07 (C-2'), 40.50 (2C, C-1, C-2), 32.98 (2C, C-3', C-1"), 31.91 (2C, C-14', C-12"), 29.75-29.6 (m, 14C), 29.53 (2C, C-13', C-11"), 29.35 (2C, C-6', C-4"), 28.35 (3C, (C(CH$_3$)$_3$), 27.67 (2C, C-4', C-2"), 22.68 (2C, C-15', C-13"), 14.1 (2C, C-16', C-14"). For C$_{37}$H$_{74}$N$_2$O$_3$ calculated: relative molecular mass 595.0; monoisotopic mass 594.6; found MS: (ESI) m/z: 595.6 ([M+H]$^+$) (25); 617.6 ([M+Na]$^+$) (100); 618.6 ([M+H+Na]$^{2+}$) (30); 1212.1 ([2M+Na]$^+$) (50); 1213.1 ([2M+H+Na]$^{2+}$) (40) HR-MS: for C$_{37}$H$_{75}$N$_2$O$_3$ calculated m/z: 595.57722. found m/z: 595.57741. for C$_{37}$H$_{74}$N$_2$O$_3$Na calculated m/z: 617.55917. found m/z: 617.55924.

Example 3

To a stirred solution of 2-tetradecylhexadecanoylchloride (general formula V; 0.39 g; 0.83 mmol) in dichloromethane (25 ml) N-tert-butoxykarbonyl-1,3-diaminopropane-hydrochloride ((CH$_3$)$_3$C—O—(C=O)—HN—(CH$_2$)$_n$—NH$_2$HCl, n=3; 186 mg, 0.88 mmol) and N,N-diisopropylethylamine (240 µl) were added and the mixture was stirred at room temperature overnight. Then the mixture was diluted with dichloromethane (50 ml) and the obtained solution was washed with aq. NaHSO$_4$ (5%; 2×15 ml) and H$_2$O (2×15 ml). The organic layer was dried over anhydrous MgSO$_4$ and concentrated in vacuo. The crude products were purified by flash chromatography on silica gel column (110 ml) in toluene-ethyl acetate (gradient 0-42% ethyl acetate, 14 ml/min, 64 min, sample was applied to the column in chloroform). Homogenous fractions of the product was evaporated in vacuo and lyophilized from dioxane to give 460 mg (94% yield) of N$^2$-(2-tetradecylhexadecanoyl)-N$^3$-tert-butoxycarbonyl-1,3-diaminopropane (general formula VI; where $n_1$=13 and X=polymethylene linker of the general formula II, where $n_2$=3). IR (CHCl$_3$): ν=3347 (NH), 3308 (NH), 2953, 2919, 2850, 1684 (C=O; Boc), 1644 (Amide I), 1544 (Amide II), 1526 (Amide II), 1467, 1447, 1390 (CH$_3$; Boc), 1365 (CH$_3$; Boc), 1277, 1248, 1175, 940, 870, 720 cm$^{-1}$; $^1$H NMR (400 MHz, CDCl$_3$): δ=6.20 (s, N$^1$H); 4.98 (s, N$^3$H); 3.31 (dt, J=6, 5.7 Hz, 2H, H-1); 3.16 (t, J=5.7 Hz, 2H, H-3); 2.04 (spt, J=4.7 Hz, H-2'); 1.64-1.56 (m, 4H, H-3', H-1', H-2); 1.44 (s, 9H, 3×CH$_3$); 1.41-1.36 (m, 2H, H-3', H-1"); 1.30-1.20 (m, 48H, 24×CH$_2$); 0.87 (t, J=7.4 Hz, 6H, H-16', H-14"); $^{13}$C NMR (100 MHz, CDCl$_3$): δ=176.65 (C-1'), 156.63 (N$^3$C), 79.33 (C(CH$_3$)$_3$), 48.09 (C-2'), 36.98 (C-1), 35.55 (C-3), 33.08 (2C, C-3', C-1"), 31.91 (2C, C-14', C-12"), 30.44 (C-2), 29.80-29.60 (m, 14C), 29.54 (2C, C-13', C-11"), 29.35 (2C, C-6', C-4"), 28.38 (3C, (C(CH$_3$)$_3$), 27.62 (2C, C-4', C-2"), 22.68 (2C, C-15', C-13"), 14.1 (2C, C-16', C-14"). For C$_{38}$H$_{76}$N$_2$O$_3$ calculated relative molecular mass 609.0; monoisotopic mass 608.6. found: MS: (ESI) m/z: 609.6. ([M+H]$^+$) (100); 631.6 ([M+Na]$^+$) (100); 632.6 ([M+H+Na]$^{2+}$) (40); 1218.2 ([2M+H]$^+$) (20); 1240.2 ([2M+H+Na]$^{2+}$) (40) HR-MS: for C$_{38}$H$_{77}$N$_2$O$_3$ calculated m/z: 609.59287. found m/z: 609.59311. for C$_{38}$H$_{76}$N$_2$O$_3$Na calculated m/z: 631.57482. found m/z: 631.57487.

Example 4

To a stirred solution of 2-tetradecylhexadecanoylchloride (general formula V; 0.5 g; 1.06 mmol) in dichloromethane (30 ml) 1-(tert-butyloxycarbonyl-amino)-3,6-dioxa-8-octaneamine ((CH$_3$)$_3$C—O—(C=O)—HN—(CH$_2$)$_2$—[O—(CH$_2$)]$_n$—O—(CH$_2$)$_2$NH$_2$, n=1; 260 mg, 0.96 mmol) and subsequently N,N-diisopropylethylamine (310 µl) were added and the mixture was stirred at room temperature overnight. Then the mixture was diluted with dichloromethane (60 ml) and the obtained solution was washed with aq. NaHSO$_4$ (5%; 2×19 ml) and H$_2$O (2×19 ml). The organic layer was dried over anhydrous MgSO$_4$ and concentrated in vacuo. The crude products were purified by flash chromatography on silica gel column (110 ml) in toluene-ethyl acetate (gradient 0-84% ethyl acetate, 15 ml/min, 44 min, sample was applied to the column in chloroform). Homogenous fractions of the product was evaporated in vacuo and finally lyophilized from dioxane to give 650 mg (90% yield) of N$^1$-(2-tetradecylhexadecanoyl)-N$^8$-tert-butoxycarbonyl-1,8-diamino-2,6-dioxaoctane (general formula VI; where $n_1$=13 and X=polyethylene glycol linker of the general formula III; where $n_3$=1). IR (CHCl$_3$): ν=3364 (NH), 3292 (NH), 2954, 2919, 2850, 1687 (C=O; Boc), 1644 (Amide I), 1552 (Amide II), 1532 (Amide II), 1466, 1391 (CH$_3$; Boc), 1365 (CH$_3$; Boc), 1282, 1255, 1178, 1137, 1115, 1034, 870, 721 cm$^{-1}$; $^1$H NMR (400 MHz, CDCl$_3$): δ=7.35 (s, N$^1$H); 6.04 (s, N$^8$H); 3.61 (dt, J=4.7 Hz, 4H, H-2, H-7); 3.55 (t, J=5.1 Hz, 4H, H-4, H-5); 3.48 (dt, J=4.7 Hz, 2H, H-8); 3.31 (t, J=5.1 Hz, 2H, H-1); 2.05 (spt, J=4.7 Hz, H-2'); 1.64-1.54 (m, 2H, H-3', H-1"); 1.45 (s, 9H, 3×CH$_3$); 1.41-1.35 (m, 2H, H-3', H-1"); 1.30-1.20 (m, 48H, 24×CH$_2$); 0.87 (t, J=7.4 Hz, 6H, H-16', H-14"); $^{13}$C NMR (100 MHz, CDCl$_3$): δ=176.65 (C-1'), 156.11 (N$^8$C), 79.54 (C(CH$_3$)$_3$), 70.38-70.11 (m, 4C, C-2, C-4, C-5, C-7), 47.85 (C-2'), 40.48 (C-8), 39.29 (C-1), 33.05 (2C, C-3', C-1"), 31.91 (2C, C-14', C-12"), 29.75-29.60 (m, 14C), 29.57 (2C, C-13', C-11"), 29.35 (2C, C-6', C-4"), 28.38 (3C, (C(CH$_3$)$_3$), 27.62 (2C, C-4', C-2"), 22.68 (2C, C-15', C-13"), 14.1 (2C, C-16', C-14″). For $C_{41}H_{82}N_2O_5$ calculated relative molecular mass 683.1; monoisotopic mass 682.6; found MS: (ESI) m/z: 683.6 ([M+H]$^+$) (10); 705.6 ([M+Na]$^+$) (100); 1388.2 ([2M+H]$^+$) (20); 1240.2 ([2M+Na]$^+$) (15); HR-MS: for $C_{41}H_{83}N_2O_5$ calculated m/z: 683.62967. found m/z: 683.62995. for $C_{41}H_{82}N_2O_5Na$ calculated m/z: 705.61159. found m/z: 705.61178.

Example 5

2-Tetradecylhexadecanoic acid (111 mg; 0.245 mmol), HATU (1-[bis(dimethylamino)methylene]-1H-1,2,3-triazolo[4,5-b]pyridinium-3-oxide-hexafluorophosphate; 100 mg; 0.262 mmol), N,N-dimethylaminopyridine (catalytic amount) were dried in vacuo (20 Pa) for 4 h. The apparatus was flushed with argon and dry N,N-dimethylformamide (4 ml) and N-methylmorpholine (50 µl) were added The reaction mixture was stirred 1 h at room temperature. 1-(tert-butoxycarbonyl-amino)-3,6-dioxa-8-octaneamine (($CH_3$)$_3$C—O—(C=O)—HN—($CH_2$)$_2$—[O—($CH_2$)$_n$]—O—($CH_2$)$_2NH_2$, n=1; 50 µl, 0.242 mmol) and dichloromethane (10 ml) were added and stirring was continued overnight at room temperature. Solvents were evaporated in vacuo (20 Pa) and the residue was dissolved in dichloromethane (15 ml). The obtained solution was washed with saturated aq. $NaHCO_3$ (2×10 ml), 5% aq. $NaHSO_4$ (2×10 ml) and $H_2O$ (2×10 ml). The organic layer was dried over anhydrous $MgSO_4$ and concentrated in vacuo. The residue was co-distilled with dioxane (3×10 ml). The crude product was purified by flash chromatography on silica gel column (120 ml) in toluene-ethyl acetate (gradient 0-50% ethyl acetate, 14 ml/min, 84 min). The homogenous fraction was evaporated in vacuo and the obtained residue was lyophilized from dioxane, to give 148 mg (90% yield) of $N^1$-(2-tetradecylhexadecanoyl)-$N^8$-tert-butoxycarbonyl-1,8-diamino-2,6-dioxaoctane (general formula VI; where $n_1$=13 and X=polyethylene glycol linker of the general formula III; where $n_3$=1), identical with the product obtained by the process described in the Example 4.

Example 6

The solution of $N^1$-(2-tetradecylhexadecanoyl)-AP-tert-butoxycarbonyl-1,2-diaminoethane (general formula VI; where $n_1$=13 and X is polymethylene linker of the general formula II, where $n_2$=2; 420 mg, 0.71 mmol) was stirred in a mixture of dichloromethane (12 ml) and trifluoroacetic acid (1.5 ml) at room temperature for 3 h. The solvents were distilled off. The residue was co-distilled with dichloromethane (3×3 ml) and subsequently dried in vacuo (20 Pa) for 8 hours. The dry residue was lyophilized from dioxane to give 430 mg (100% yield) of $N^1$-(2-tetradecylhexadecanoyl)-1-amino-2-amoniumethane-trifluorotacetate (general formula VII; where $n_1$=13 and X=polymethylene linker of the general formula II, where $n_2$=2). For $C_{32}H_{66}N_2O$ calculated: relative molecular mass 494.9; monoisotopic mass 494.5; found: MS: (ESI) m/z: 495.5, ([M+H]$^+$) (100); 517.5 ([M+Na]$^+$) (30); HR-MS: for $C_{32}H_{67}N_2O$ calculated m/z: 495.52479. found m/z: 495.52480.

Example 7

The solution $N^1$-(2-tetradecylhexadecanoyl)-$N^3$-tert-butoxycarbonyl-1,3-diaminopropane (general formula VI; where $n_1$=13 and X=polymethylene linker of the general formula II, where $n_2$=3; 359 mg; 0.69 mmol) was stirred in a mixture of dichloromethane (12 ml) and trifluoroacetic acid (1.5 ml) at room temperature for 3 h. The solvents were distilled off. The residue was co-distilled with dichloromethane (3×3 ml) and subsequently dried in vacuo (20 Pa) for 8 hours. The dry residue was lyophilized from dioxane to give 430 mg (100% yield) of $N^1$-(2-tetradecylhexadekanoyl)-1-amino-3-amoniumpropane-trifluoroacetate (general formula VII; where $n_1$=13 and X=polymethylene linker of the general formula II, where $n_2$=3). For $C_{33}H_{68}N_2O$ calculated: relative molecular mass 508.9; monoisotopic mass 508.5. found MS: (ESI) m/z: 509.5, ([M+H]$^+$) (100); HR-MS: for $C_{33}H_{69}N_2O$ calculated m/z: 509.54044. found m/z: 509.54046.

Example 8

The solution of $N^1$-(2-tetradecylhexadecanoyl)-$N^8$-tert-butoxycarbonyl-1,8-diamino-2,6-dioxaoctane (general formula VI; where $n_1$=13 and X=polyethylene glycol linker of the general formula III; where $n_3$=1; 680 mg; 1 mmol) was stirred in a mixture of dichloromethane (12 ml) and trifluoroacetic acid (2 ml) at room temperature for 3 h. The solvents were distilled off, the residue was co-distilled with dichloromethane (3×3 ml) and subsequently dried in vacuo (20 Pa) for 8 hours. The dry residue was lyophilized from dioxane to give 696 mg (100% yield) of $N^1$-(2-tetradecylhexadecanoyl)-1-amino-8-ammonium-2,6-dioxaoctane-trifluoroacetate (general formula VII; where $n_1$=13 and X=polyethylene glycol linker of the general formula III; where $n_3$=1) in quantitative yield. For $C_{36}H_{74}N_2O_3$ calculated: relative molecular mass 583.0; monoisotopic mass 582.6; found: MS: (ESI) m/z: 583.6 ([M+H]$^+$) (100); 605.6 ([M+Na]$^+$) (40); HR-MS: for $C_{36}H_{75}N_2O_3$ calculated m/z: 583.57722. found m/z: 583.57721. for $C_{36}H_{74}N_2O_3Na$ calculated m/z: 605.55971. found m/z: 605.55905.

Example 9

To a stirred solution of $N^1$-(2-tetradecylhexadecanoyl)-1-amino-2-amoniumethane-trifluorotacetate (general formula VII; where $n_1$=13 and X=polymethylene linker of the general formula II, where $n_2$=2; 135 mg, 0.22 mmol) in dichloromethane (10 ml), N,N-dimethylaminopyridine (38 mg; 0.31 mmol), N-tert-butoxycarbonyl-aminooxyacetic acid (58 mg; 0.27 mmol) and 1,3-diisopropylcarbodiimide (41 µl; 0.26 mmol) were added and the mixture was stirred at room temperature overnight. The reaction mixture was diluted with dichloromethane (15 ml) and the obtained solution was washed with saturated aq. $NaHCO_3$ (2×10 ml), 5% aq. $NaHSO_4$ (2×10 ml), $H_2O$ (2×10 ml). The organic layer was collected, dried over anhydrous $MgSO_4$ and concentrated in vacuo. The crude products were purified by flash chromatography on silica gel column (100 ml) in toluene-ethyl acetate. (gradient 10-73% ethyl acetate, 14 ml/min, 74 min, applied in $CHCl_3$). The homogenous fractions of the products were evaporated in vacuo and finally lyophilized from dioxane to give 126 mg (86% yield) of $N^1$-(2-tetradecylhexadecanoyl)-AP-(N-tert-butoxycarbonylamiooxyacetyl)-1,2-diaminoethane (general formula VIII; where $n_1$=13 and X=polymethylene linker of the general formula II, where $n_2$=2). IR ($CHCl_3$): ν=3392 (NH), 3280 (NH), 3099, 2954, 2919, 2850, 1755 (C=O; Boc), 1726 (C=O; Boc), 1645 (Amide I), 1551 (Amide II), 1467, 1447, 1390 ($CH_3$; Boc), 1368 ($CH_3$; Boc), 1283, 1253, 1234, 1164, 1105, 1048, 1014, 973, 761, 719 cm$^{-1}$; $^1$H NMR (400 MHz, $CDCl_3$): δ=8.23 (s, $N^1$H); 7.84 (s, $N^2$H); 6.39 (s, $NHCO_2$); 3.45 (s, 4H, H-1, H-2); 2.04 (sot, J=4.7 Hz, H-2′); 1.6-1.54 (m, 2H, H-3′, H-1″); 1.49 (s, 9H, 3×$CH_3$); 1.43-1.35 (m, 2H, H-3′, H-1"); 1.32-1.18 (m, 48H, 24×CH$_2$); 0.87 (t, J=7.0 Hz, 6H, H-16', H-14"); $^{13}$C NMR (100 MHz, CDCl$_3$): δ=177.42 (C-1'), 169.83 (N$^2$C), 157.71 (NHCO$_2$) 83.11 (C(CH$_3$)$_3$), 76.42 (C=OCH$_2$O); 48.01 (C-2'), 39.60 (2C, C-1, C-2), 32.93 (2C, C-3', C-1"), 31.91 (2C, C-14', C-12"), 29.75-29.6 (m, 14C), 29.53 (2C, C-13', C-11"), 29.35 (2C, C-6', C-4"), 28.15 (3C, (C(CH$_3$)$_3$), 27.66 (2C, C-4', C-2"), 22.68 (2C, C-15', C-13"), 14.11 (2C, C-16', C-14"). For C$_{39}$H$_{77}$N$_3$O$_5$ calculated relative molecular mass 668.1; monoisotopic mass 667.6 MS: (ESI) m/z: 690.6 ([M+Na]$^+$) (100); 691.6 ([M+H+Na]$^{2+}$) (40); HR-MS: for C$_{39}$H$_{78}$N$_3$O$_5$ calculated m/z: 668.59360. found m/z: 668.59363. for C$_{39}$H$_{77}$N$_3$O$_5$Na calculated m/z: 690.57554. found m/z: 690.57564.

Example 10

To a stirred solution of N$^1$-(2-tetradecylhexadecanoyl)-1-amino-3-ammoniumpropane-trifluoroacetate (general formula VII; where n$_1$=13 and X=polymethylene linker of the general formula II, where n$_2$=3; 181 mg; 0.29 mmol) in dichloromethane (13 ml), N,N-dimethylaminopyridine (50 mg; 0.36 mmol), N-tert-butoxycarbonyl-aminooxyacetic acid (76 mg; 0.35 mmol) and 1,3-diisopropylcarbodiimide (56 µl; 0.36 mmol) were added and the mixture was stirred at room temperature overnight. The reaction mixture was diluted with dichloromethane (18 ml) and the obtained solution was washed with saturated aq. NaHCO$_3$ (2×16 ml), 5% aq. NaHSO$_4$ (2×16 ml), H$_2$O (2×16 ml). The organic layer was collected, dried over anhydrous MgSO$_4$ and concentrated in vacuo. The crude products were purified by flash chromatography on silica gel column (100 ml) in toluene-ethyl acetate (gradient 10-73% ethyl acetate, 14 ml/min, 74 min). The homogenous fractions of the products were evaporated in vacuo and finally lyophilized from dioxane to give 174 mg (88% yield) of N$^1$-(2-tetradecylhexadecanoyl)-N$^3$—(N-tert-butoxycarbonylamiooxyacetyl)-1,3-diaminopropane (general formula VIII; where n$_1$=13 and X=polymethylene linker of the general formula II, where n$_2$=3). IR (CHCl$_3$): ν=3392 (NH), 3280 (NH), 3086, 2954, 2919, 2850, 1755 (C=O; Boc), 1726 (CH$_3$; Boc), 1645 (Amide I), 1544 (Amide II), 1467, 1437, 1393 (CH$_3$; Boc), 1368 (CH$_3$; Boc), 1271, 1252, 1173, 1132, 1050, 1016, 984, 758, 719 cm$^{-1}$; $^1$H NMR (400 MHz, CDCl$_3$): δ=8.24 (s, N$^1$H); 8.1 (s, N$^3$H); 6.53 (s, NHCO$_2$); 4.33 (dt, 2H, J=6, 5.7 Hz, H-1); 3.29 (dt, 2H, J=6, 5.7 Hz, H-3); 2.06 (spt, J=4.7 Hz, H-2'); 1.68 (tt, 2H, J=4.7, 4.7 Hz, H-2); 1.6-1.54 (m, 2H, H-3', H-1"); 1.47 (s, 9H, 3×CH$_3$); 1.43-1.37 (m, 2H, H-3', H-1"); 1.32-1.18 (m, 48H, 24×CH$_2$); 0.87 (t, J=7.0 Hz, 6H, H-16', H-14"); $^{13}$C NMR (100 MHz, CDCl$_3$): δ=176.96 (C-1'), 169.75 (N$^3$C), 157.78 (NHCO$_2$) 82.89 (C(CH$_3$)$_3$), 75.95 (C=OCH$_2$O); 48.10 (C-2'), 35.44 (C-1), 35.23 (C-3), 33.02 (2C, C-3', C-1"), 31.91 (2C, C-14', C-12"), 29.75-29.6 (m, 14C), 29.54 (2C, C-13', C-11"), 29.35 (2C, C-6', C-4"), 29.21 (C-2), 28.09 (3C, (C(CH$_3$)$_3$), 27.70 (2C, C-4', C-2"), 22.67 (2C, C-15', C-13"), 14.11 (2C, C-16', C-14"). For C$_{40}$H$_{29}$N$_3$O$_5$ calculated relative molecular mass 682.1; monoisotopic mass 681.6; found MS: (ESI) m/z: 704.6 ([M+Na]$^+$) (100); 405.6 ([M+H+Na]$^{2+}$) (40); HR-MS: for C$_{40}$H$_{80}$N$_3$O$_5$ calculated m/z: 682.60925. found m/z: 682.60931. for C$_{40}$H$_{29}$N$_3$O$_5$Na calculated m/z: 704.59119. found m/z: 704.59123.

Example 11

To a stirred solution of N$^1$-(2-tetradecylhexadecanoyl)-1-amino-8-ammonium-2,6-dioxaoctane-trifluoroacetate (general formula VII; where n$_1$=13 and X=polyethylene glycol linker of the general formula III; where n$_3$=1; 414 mg, 0.575 mmol) in dichloromethane (3.5 ml), N,N-dimethylaminopyridine (98 mg; 0.8 mmol), N-tert-butoxycarbonyl-aminooxyacetic acid (151 mg; 0.69 mmol) and 1,3-diisopropylcarbodiimide (110 µl; 0.71 mmol) were added and the mixture was stirred at room temperature overnight. The reaction mixture was diluted with dichloromethane (40 ml) and the obtained solution was washed with saturated aq. NaHCO$_3$ (2×35 ml), 5% aq. NaHSO$_4$ (2×35 ml), H$_2$O (2×35 ml). The organic layer was dried over anhydrous MgSO$_4$. and concentrated in vacuo. The crude products were purified by flash chromatography on silica gel column (100 ml) in toluene-ethyl acetate (gradient 10-100% ethyl acetate, 14 ml/min, 74 min, applied in CHCl$_3$). The homogeneous fractions of the products were evaporated in vacuo and finally lyophilized from dioxane to give 370 mg (85% yield) of N$^1$-(2-tetradecylhexadecanoyl)-N$^8$—(N-tert-butoxycarbonylamiooxyacetyl)-1,8-diamino-2,6-dioxaoctane (general formula VIII; where n$_1$=13 and X=polyethylene glycol linker of the general formula III; where n$_3$=1). IR (CHCl$_3$): ν=3392 (NH), 3292 (NH), 3090, 2954, 2919, 2850, 1756 (C=O; Boc), 1644 (Amide I), 1551 (Amide II), 1467, 1425, 1394 (CH$_3$; Boc), 1368 (CH$_3$; Boc), 1321, 1273, 1251, 1166, 1137, 1115, 1034, 980, 854, 758, 721, 594 cm$^{-1}$; $^1$H NMR (400 MHz, CDCl$_3$): δ=8.07 (s, N$^1$H); 7.99 (s, N$^8$H); 6.22 (s, NHCO$_2$); 3.62 (s, 4H, H-4, H-5); 3.59 (t, J=5.4 Hz, 2H, H-7); 3.55 (t, J=5.3 Hz, 2H, H-2); 3.51 (dt, J=5.5 Hz, J=5.3 Hz 2H, H-1); 3.45 (dt, J=5.5 Hz, J=5.0 Hz 2H, H-1); 2.06 (spt, J=4.8 Hz, H-2'); 1.6-1.54 (m, 2H, H-3', H-1"); 1.47 (s, 9H, 3×CH$_3$); 1.43-1.37 (m, 2H, H-3', H-1"); 1.32-1.18 (m, 48H, 24×CH$_2$); 0.87 (t, J=7.0 Hz, 6H, H-16', H-14"); $^{13}$C NMR (100 MHz, CDCl$_3$): δ=176.47 (C-1'), 168.92 (N$^8$C), 157.56 (NHCO$_2$) 82.77 (C(CH$_3$)$_3$), 75.99 (C=OCH$_2$O); 70.28 (1C, C4); 70.25 (1C, C-5); 70.13 (2C, C-2, C-7); 47.90 (C-2'); 39.04 (1C, C-8); 38.75 (1C, C-1); 33.02 (2C, C-3', C-1"), 31.91 (2C, C-14', C-12"), 29.75-29.6 (m, 14C), 29.57 (2C, C-13', C-11"), 29.34 (2C, C-6', C-4"), 28.09 (3C, (C(CH$_3$)$_3$), 27.70 (2C, C-4', C-2"), 22.67 (2C, C-15', C-13"), 14.11 (2C, C-16', C-14"). For C$_{43}$H$_{85}$N$_3$O$_2$ calculated: relative molecular mass 755.2; monoisotopic mass 755.6; found MS: (ESI) m/z: 756.6 ([M+H]$^+$) (5); 778.6 ([M+Na]$^+$) (100); HR-MS: for C$_{43}$H$_{86}$N$_3$O$_2$ calculated m/z: 756.64603. found m/z: 756.64616. for C$_{43}$H$_{85}$N$_3$O$_7$Na calculated m/z: 778.62797. found m/z: 778.62805.

Example 12

N$^1$-(2-tetradecylhexadecanoyl)-N$^2$—(N-tert-butoxycarbonylamiooxyacetyl)-1,2-diaminoethane (general formula VII; where n$_1$=13 and X=polymethylene linker of the general formula II, where n$_2$=2; 202 mg, 0.3 mmol) was stirred in a mixture of dichloromethane (8 ml) and trifluoroacetic acid (8 ml) at room temperature for 2.5 h. The solvents were distilled off in vacuo. The residue was co-distilled with dichloromethane (3×4 ml), dried in vacuo (20 Pa), and subsequently lyophilized from dioxane to give 200 mg (97% yield) of N$^1$-(2-tetradecylhexadecanoyl)-N$^2$-amoniumoxyacetyl-1,2-diaminoethane-trifluoroacetate (general formula I; where n$_1$=13 and X=polymethylene linker of the general formula II, where n$_2$=2). For C$_{34}$H$_{69}$N$_3$O$_3$ calculated: relative molecular mass 567.9; monoisotopic mass 567.5; found: MS: (ESI) m/z: 575.5 ([M-NH$_2$+H+Na]$^+$) (100); HR-MS: for C$_{34}$H$_{70}$N$_3$O$_3$ calculated m/z: 568.54117. found m/z: 568.54138. for C$_{34}$H$_{69}$N$_3$O$_3$Na calculated m/z: 590.52311. found m/z: 590.52322.

Example 13

N$^1$-(2-tetradecylhexadecanoyl)-N$^3$—(N-tert-butoxycarbonylamiooxyacetyl)-1,3-diaminopropane (general formula VIII; where $n_1=13$ and X=polymethylene linker of the general formula II, where $n_2=3$; 87 mg, 0.13 mmol) was stirred in a mixture of dichloromethane (3.5 ml) and trifluoroacetic acid (3.5 ml) at room temperature for 2.5 h. The solvents were distilled, the residue was co-distilled with dichloromethane (3×2 ml) and subsequently dried in vacuo (20 Pa) for 8 hours. The residue was lyophilized from dioxane, to give 87 mg (99% yield) of $N^1$-(2-tetradecylhexadecanoyl)-$N^3$-amoniumoxyacetyl-1,3-diaminopropane-trifluoracetate (general formula I; where $n_1=13$ and X=polymethylene linker of the general formula II, where $n_2=3$). For $C_{35}H_{71}N_3O_3$ calculated relative molecular mass 582.0; monoisotopic mass 581.6; found MS: (ESI) m/z: 604.4 ($[M+Na]^+$) (100); HR-MS: for $C_{35}H_{72}N_3O_3$ calculated m/z: 582.55682. found m/z: 582.55702. for $C_{35}H_{71}N_3O_3Na$ calculated m/z: 604.53876. found m/z: 604.53892.

Example 14

$N^1$-(2-tetradecylhexadecanoyl)-$N^8$—(N-tert-butoxycarbonylamiooxyacetyl)-1,8-diamino-2,6-dioxaoctane (general formula VIII; where $n_1=13$ and X=polyethylene glycol linker of the general formula III; where $n_3=1$; 345 mg, 0.13 mmol) was stirred in a mixture of dichloromethane (14 ml) and trifluoroacetic acid (14 ml) at room temperature for 2.5 h. The solvents were distilled off, the residue was co-distilled with dichloromethane (3×8 ml) and subsequently dried in vacuo for 8 hours. The residue was lyophilized from dioxane, to give 330 mg (98% yield) of $N^1$-(2-tetradecylhexadecanoyl)-$N^3$-amoniumoxyacetyl-1,3-diamino-2,6-dioxaoctane-trifluoracetate I (where $n_1=13$ and X=polyethylene glycol linker of the general formula III, where $n_3=1$). For $C_{38}H_{77}N_3O_5$ calculated: relative molecular mass 656.1; monoisotopic mass 655.6; found MS: (ESI) m/z: 604.4 ($[M+Na]^+$) (100); HR-MS: for $C_{38}H_{78}N_3O_5$ calculated m/z: 656.59360. found m/z: 656.59380. for $C_{38}H_{77}N_3O_5Na$ calculated m/z: 678.57554. found m/z: 678.57573.

Examples—surface modification of liposomes and biological activities

Example 15

Preparation of Liposomes with Incorporated Aminooxylipids of General Formula I (According to Examples 12, 13 and 14).

Methods: Liposomes with incorporated aminooxylipids were prepared by phospholipid film hydration. All lipids were dissolved in chloroform at a concentration of 10 mg of lipid/1 ml chloroform at a molar ratio of 99% EPC to 1% aminooxylipids of general formula I (according to Examples 12, 13 and 14). The chloroform solution was evaporated in a globular flask on a rotary evaporator; pressure: 100 hPa, water bath temperature: 37° C., 90 revolutions/minute). The resulting lipid film was hydrated with PBS (pH 7.2, 0.14M NaCl, 20 mM Na-phosphate) to a final concentration of 10 mg/ml. The liposomes were then extruded through Nucleopore polycarbonate filters with 400 and 100 nm pore size. The size and zeta-potential were measured using a Nanosizer ZS (Malvern, UK) in a DTS cell, Attenuator value 4, 25° C. Results: Incorporation of N-aminooxylipids of general formula I (according to Examples 12, 13 and 14) into liposomes has no significant effect on the final distribution of liposomes. Example with a lipid of general formula I (according to Example 12): EPC liposomes: size 82 nm, PDI 0.11; EPC+ aminooxylipid 1%: size 81 nm, PDI 0.1.

Aminooxylipids of general formula I (according to Examples 12, 13 and 14) are capable of forming a stable lipid bilayer with other auxiliary lipids (EPC=egg phosphatidylcholine) and therefore can be used for preparation of liposomes. The size of the liposomes corresponds with the pore size of the filter used in the extrusion. Zeta potential of the liposomes containing 1% aminooxylipid of general formula I (according to Example 12, 13 or 14) in PBS solution with neutral pH reaches the values of around 0 mV.

Example 16

Cytotoxicity of Liposomes with Incorporated Aminooxylipids of General Formula I

Methods: The cytotoxicity of liposomes prepared as described in Example 15 is determined by comparing the cytotoxicity of EPC liposomes and EPC liposomes with an incorporated aminooxylipid of general formula I (according to Example 12, 13 or 14) in in vitro experiments with T-lymphocytes and on H1299 cells of lung carcinoma cell line.

Measurements were performed on a flow cytometer Fortessa (Becton Dickinson). Apoptotic cells were detected and quantified using the fluorescent dye Annexin V (Invitrogen).

In all experiments, 500 µl media per well were used and lipid content was 100 µg per 1 ml of the medium. Unmodified liposomes and liposomes modified post-liposomally with hyaluronic acid were incubated. In Experiment 1, H1299 cells of lung carcinoma were incubated for 30 minutes at 4° C. In Experiment 2, T-lymphocytes were used and incubated at room temperature in a rotator. In Experiments 3 and 4, H1299 cells of lung carcinoma cell line were used and incubated for 2 hours in a $CO_2$ incubator (37° C., 5% $CO_2$). In Experiment 5, H1299 cells of lung carcinoma were used. These cells were incubated for 30 minutes at 4° C. in a refrigerator.

Results: The incorporation of aminooxylipids of general formula I (according to Example 12, 13 or 14) into the liposomal bilayer does not result in an increase in their cytotoxicity. Non-toxicity was demonstrated by comparing the cytotoxicity of EPC liposomes and EPC liposomes with an incorporated aminooxylipid of general formula I (according to Example 12, 13 or 14) in in vitro experiments using T-lymphocytes and
H1299 cells of lung carcinoma cell line.
Data is shown in Table 1.

TABLE 1

| Experiment | Apoptotic cells (%) | | |
| --- | --- | --- | --- |
| | control | EPC-lip | N-oxy-lip |
| 1 | 0 | 0.1 | 0.1 |
| 2 | 0.1 | 0 | 0.1 |
| 3 | 0 | 0 | 0 |
| 4 | 0 | 0 | 0 |
| 5 | 0 | 0.1 | 0.3 |

Example 17

Preparation of Liposomes with HA Coupled Through the Reducing End of its Molecule; Modification of Liposome Size with 1% Aminooxylipid of General Formula I (According to Example 12, 13 or 14) after Binding of HA; DLS and TEM Images of the Structure of HA-Conjugated Liposomes Methods: Liposomes prepared according to the procedure described in Example 15, containing 1% aminoxylipid of general formula I (according to Example 12, 13 or 14) at a starting concentration of 10 mg/ml PBS were mixed with HA (Mw 10440, Contipro) at a concentration of 1 mg/ml PBS in a ratio of 1 mg total lipid to 0.1 mg HA. Incubation takes place for at least 30 minutes at room temperature. The excess HA was removed by gel chromatography on a Superose 6 column (Pharmacia).

DLS measurements were carried out under the same conditions as in Example 15.

For TEM (Philips 208S Morgagni, FEI, Czech Republic), specimens were stained with ammonium molybdate (1% solution), for SEM (Hitachi SU 8010, Hitachi Ltd., Japan), specimens were not stained, and for CryoTEM, counter-staining with uranyl acetate ($UO_2^{+2}$; 0.05%) was used due to its selective electrostatic binding to HA.

Results: Measurement by DLS

Figure 1:
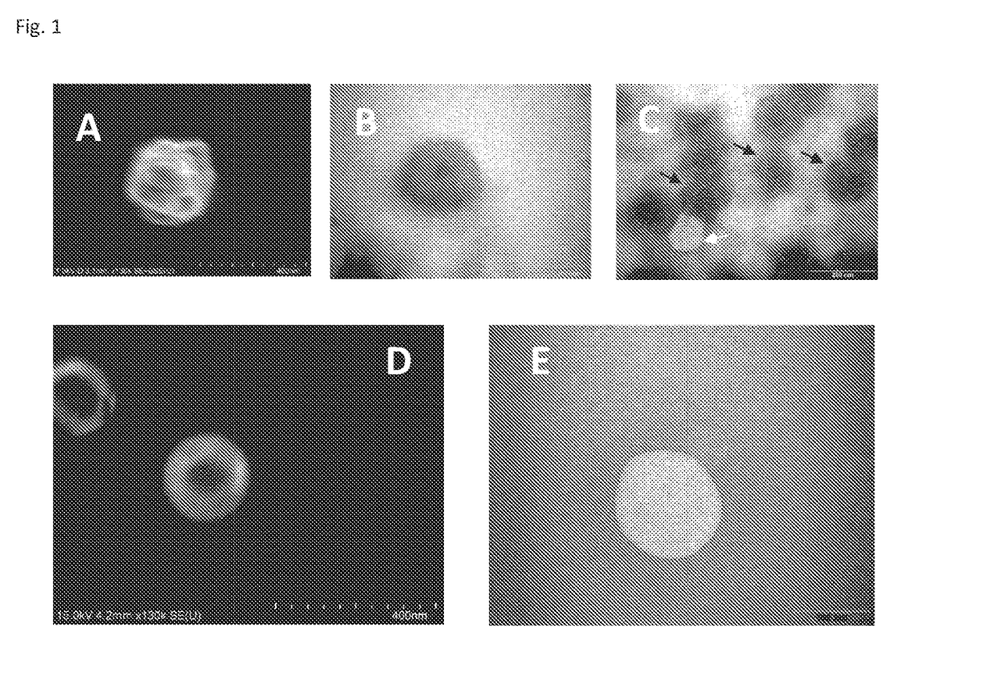
FIG. 1: SEM and TEM micrographs of liposomes: SEM of a hyaluronic acid-coated liposome (A); TEM of a hyaluronic acid-coated liposome (staining with ammonium molybdate) (B); TEM of a mixture of hyaluronic acid-coated liposomes and unmodified liposomes (staining with ammonium molybdate), modified liposomes (black arrows), an unmodified liposome (white arrow) (C); SEM of an unmodified liposome (D); TEM of an unmodified liposome (E).
Figure 2:
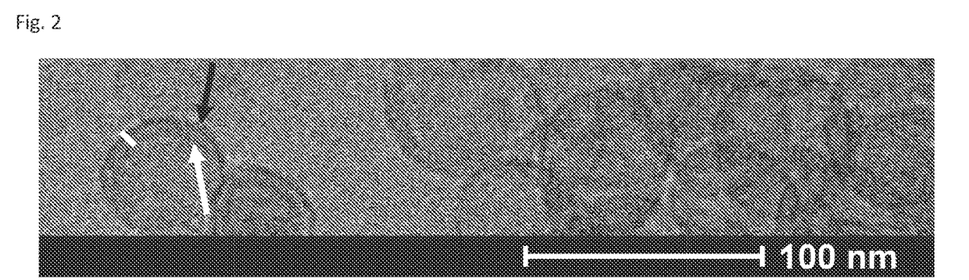
FIG. 2: CryoTM image of liposomes with HA bound using oxime ligation.

Hyaluronic acid 5-15 kDa: size 5-6 nm; unmodified liposomes: size 71 nm; HA-conjugated liposomes: size 82 nm; ζ-potential of empty liposomes was 0.4 mV, after HA (Mw 10440) binding, it decreased to −4.4 mV. Results from TEM and SEM (FIG. 1); a brush structure composed of linear HA fibres is visible, see arrows. CryoTEM results (FIG. 2); the outer HA layer is more contrasting due to the $UO_2^{+2}$ bond (black arrow). The layer is 3.5-6.7 nm thick, which is in good agreement with the hydrodynamic diameter of the HA molecule. The inner layer (white arrow) is a phospholipid bilayer which is 3.7-4.2 nm thick. The increase in liposome size (measured by DLS) is approximately 7-12 nm, which is in good agreement with data obtained by CryoTEM (a white line segment 10 nm long).

Example 18

Preparation of Liposomes with Encapsulated Hyaluronic Acid with Mw 391 kDa Via the Reducing End of its Molecule Methods: Liposomes prepared according to the procedure described in Example 15, containing 1% aminooxylipid of general formula I (according to Example 12, 13 or 14) at a starting concentration of 10 mg/ml PBS were mixed with HA (Mw 391 kDa, Contipro) at a concentration of 1 mg/ml PBS in a ratio of 1 mg total lipid to 0.1 mg HA. Incubation is carried out for at least 30 minutes at room temperature. The excess HA was removed by gel chromatography on Superose 6 column (Pharmacia).

Results: ζ-potential of empty liposomes is −0.4 mV and after addition of HA (Mw 391 KDa) it decreased to −7 mV. The increase in the size of HA-modified liposomes is 20 nm. TEM images confirm the binding of HA with Mw of 391 kDa.

Example 19

Preparation of Liposomes with Fluorescently Labelled HA

Methods: Liposomes prepared according to the procedure described in Example 15, containing 1% aminooxylipid of general formula I (according to Example 12, 13 or 14) at a starting concentration of 10 mg/ml PBS were mixed with HA which was modified using FITC (Sigma-Aldrich) at a concentration of 1 mg/ml PBS in a ratio of 1 mg total lipid to 0.1 mg HA. Incubation is carried out for at least 30 minutes at room temperature. The excess HA was removed by gel chromatography on Superose 6 column (Pharmacia). The liposomes prepared in this way are further used in experiments in which the possibility of their imaging using fluorescence techniques (fluorescence microscopy, fluorimetry) is an advantage.

Example 20

Preparation of Liposomes with IgY-Linked Immunoglobulin Modified by Aldehyde Groups Generated by Oxidative Cleavage of its Carbohydrate Component and Specific Interaction of Liposomes with the Bacterium *S. aureus*

Methods: Liposomes prepared as described in Example 15, containing 1% aminoxylipidid of general formula I (according to Example 14) at a starting concentration of 10 mg/ml PBS were mixed with periodate-activated IgY in PBS in a ratio of 1 mol of aminoxylipid to 1 mol of IgY. Incubation is carried out for at least 30 minutes at room temperature. The excess of unbound IgY was removed by gel chromatography on Superose 6 column (Pharmacia). The IgY used was isolated from egg yolk produced by hens immunized with killed *S. aureus*. *S. aureus* bacteria were incubated with fluorescein-labelled IgY from eggs of immunized hens.

Figure 3:
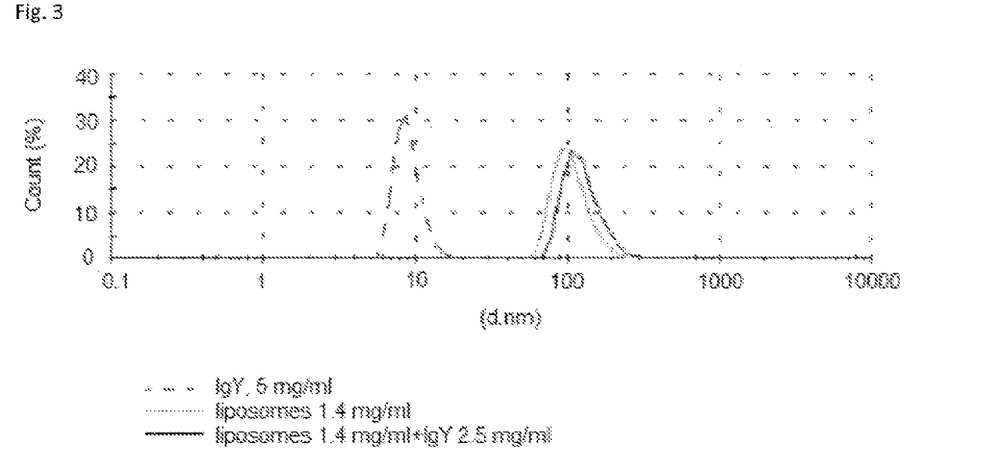
FIG. 3: Size distribution of liposomes with 1% aminooxylipid of general formula I (according to Example 14) and the same liposomes coupled with IgY. Distribution is expressed as particle numbers per category of a particular size: 107 nm for liposomes alone; 126 nm for liposomes with IgY; 9 nm for IgY.
Figure 4:
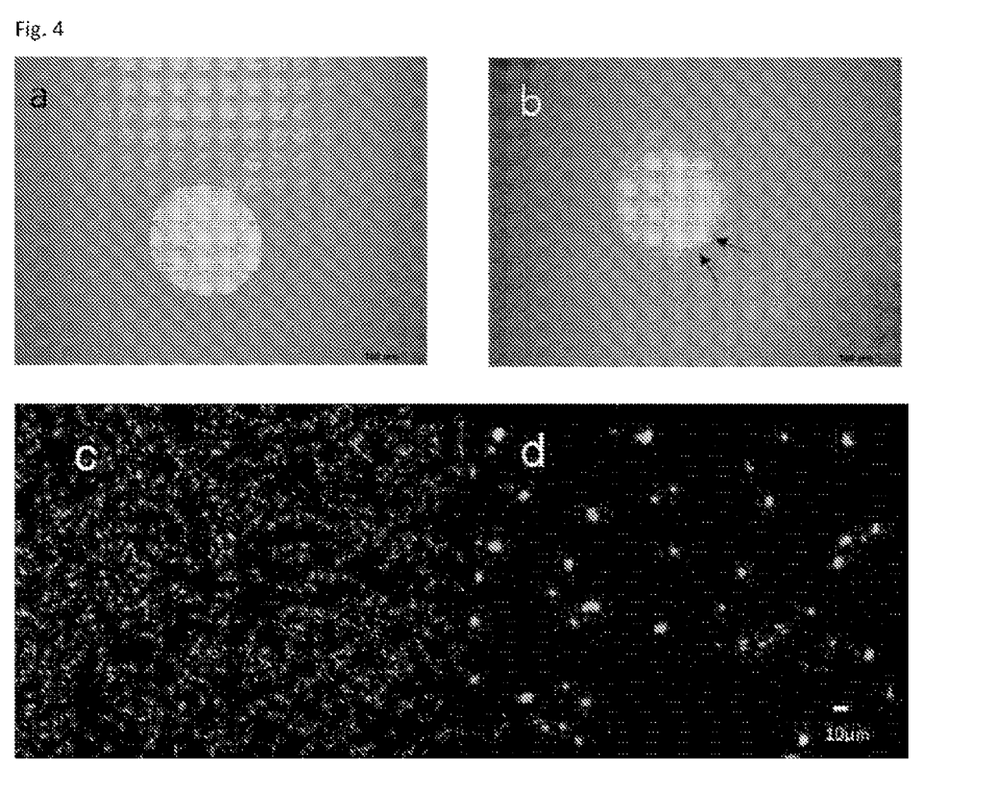

Results: A difference of approximately 19 nm between unmodified liposomes and proteoliposomes with bound IgY corresponds to the increase in liposome size due to homogeneous binding of IgY to their surface, as determined by DLS (FIG. 3) and TEM (FIG. 4a, b). The specific IgY binding to the bacteria and their labelling occurred; IgY does not have the ability to aggregate antigens and, therefore, each step is taken separately (FIG. 4c). Fluorescently-labelled liposomes (fluorescein phosphatidylethanolamine) with bound specific IgY interacted with bacteria, their fluorescence labelling and aggregation occurred (FIG. 4d). Binding to bacteria was observed by fluorescence microscopy. The result proves that the conjugation of immunoglobulins to liposomes by N-oxy ligation preserves their ability to recognize the antigen, to aggregate it and to target the therapeutics to cells (e.g., cytostatic drugs) or bacteria (antibiotics). In the case of bacteria, this system is suitable for mastitis treatment in dairy cows.

Example 21

The Binding of the Polysaccharide Mannan to Liposomes and the Stimulation of Dendritic Cells with Mannan-Coated Liposomes Methods: The liposomes prepared as described in Example 15, containing 1% aminooxylipidid of general formula I (according to Example 14) at a starting concentration of 10 mg/ml PBS were mixed with a mannan solution in PBS in a ratio of 1 mg total lipid to 0.1 mg mannan. The reaction was carried out at room temperature. Low molecular weight components and unbound mannan were removed by gel chromatography on a Superose 6 column. The mannan binding onto the liposomal surface was confirmed by: a) scanning and transmission electron microscopy; b) the change in liposome size was determined by the DLS technique (Zetasizer ZS, Malvern UK). The polysaccharide mannan was isolated from the yeast *Candida albicans*. The size of the molecules of mannan and liposomes was measured by DLS. Liposome surface modification was also demonstrated by TEM and SEM. Dendritic cells were prepared by culture from peripheral blood of healthy donors. Their stimulating activity was compared with lipopolysaccharide activity (LPS, standard *Salmonella minnesota*).

Figure 5:
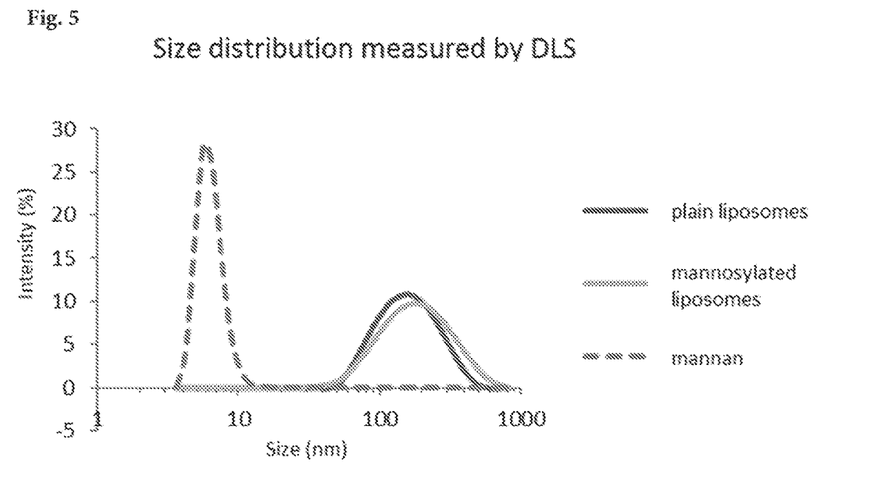
FIG. 5: Size distribution of empty vs. mannosylated liposomes: the size of empty liposomes and mannan is 145 nm and 6 nm, respectively. The size of manosylated liposomes is 155 nm; i.e. increased by 10 nm.
Figure 6:
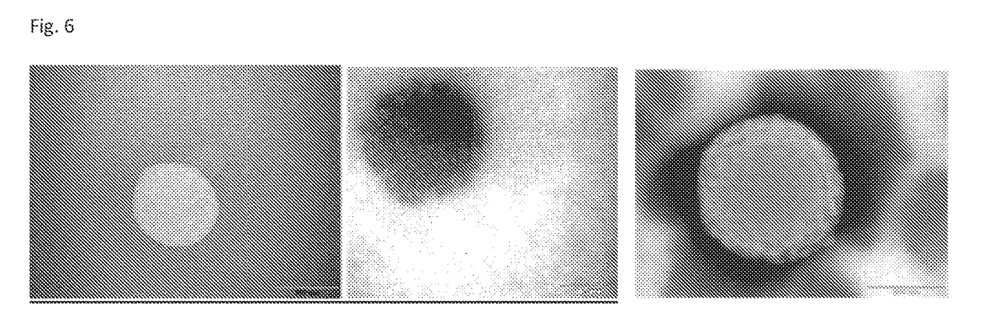
FIG. 6: Transmission electron microscopy (TEM) and scanning electron microscopy (SEM) images of liposomes: TEM image of an unmodified liposome (left), TEM image of a mannan-coated liposome (centre), SEM image of a mannan-coated liposome (right).
Figure 7:
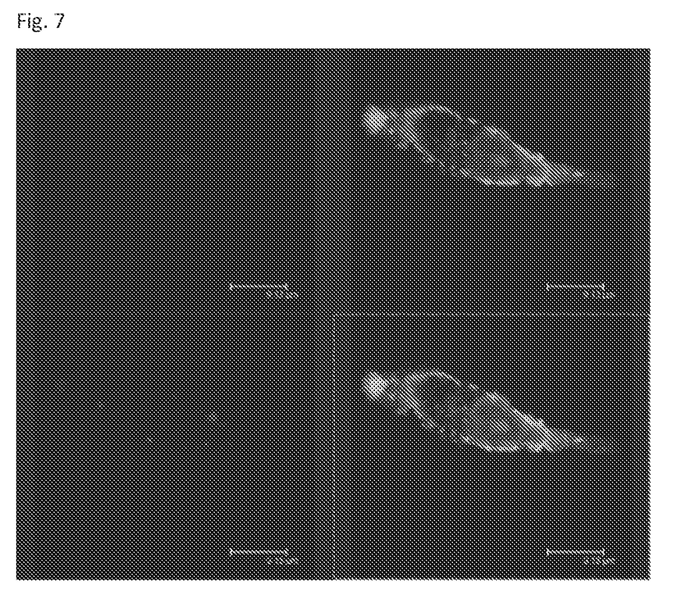
FIG. 7: Confocal microscopy images: stained nucleus (top left); stained surface HLA-DR antigen (top right); manosylated liposomes (bottom left); combination of all three images (bottom right).

Results: The mannan molecule is 6 nm in size; the size of unmodified liposomes is 145 nm, and mannan-bound liposomes 155 nm. It follows that an increase of 10 nm occurred, which is in a good correlation with the theoretically expected increase by 12 nm (twice the size of the mannan molecule). The size distribution is shown in FIG. 5. The molecules of bound mannan can be seen in electron microscopy images after negative staining with ammonium molybdate (FIG. 6). Mannan-coated liposomes retained an intense immunostimulatory activity which was demonstrated in human dendritic cells in vitro. Confocal microscopy confirmed the interaction of mannan-modified liposomes with dendritic cells (DC) and their internalisation into the cytoplasm (Table 2). Specific markers of dendritic cell activation were monitored by flow cytometry. The interaction with DC was imaged by confocal microscopy (FIG. 7).

TABLE 2

| Parameter | Control | LPS | Mannosylated liposomes |
|---|---|---|---|
| CD11c+/CD80+ | 15 | 83 | 74 |
| CD11c+/CD83+ | 45 | 88 | 83 |
| CD4+ | 0 | 15 | 15 |
| CD8+ | 0 | 21 | 24 |
| CD3+ | 0 | 17 | 17 |

Example 22

Comparison of HA Binding onto Liposomes Presenting the Aminooxy Group Vs. Liposomes Presenting the Amino Group Methods: Liposomes presenting the aminooxy group were prepared by the procedure described in Example 15, containing 1% aminooxylipidid of general formula I (according to Example 14) at a starting concentration of 10 mg/ml PBS. The amino group-presenting liposomes were prepared by the same technique with the amino group-containing lipid DOPE. These liposomes at a starting concentration of 10 mg/ml PBS were mixed with fluorescently labelled HA (Sigma-Aldrich) at a concentration of 1 mg/ml PBS in a ratio of 1 mg total lipid to 0.1 mg HA. Incubation takes place for at least 30 minutes at room temperature (see Example 19). Both samples were incubated in 10 mM citric acid. Unbound HA was removed on a Superose 6 column (200 µl spraying buffer, flow rate of the first milliliter was 0.1 ml/min, then 0.3 ml/min, collection of 1 ml fractions). Fluorescence was measured using a Perkin Elmer fluorimeter at appropriate wavelengths (excitation for FITC-HA was 490 nm, emission 505 nm).

Figure 8:
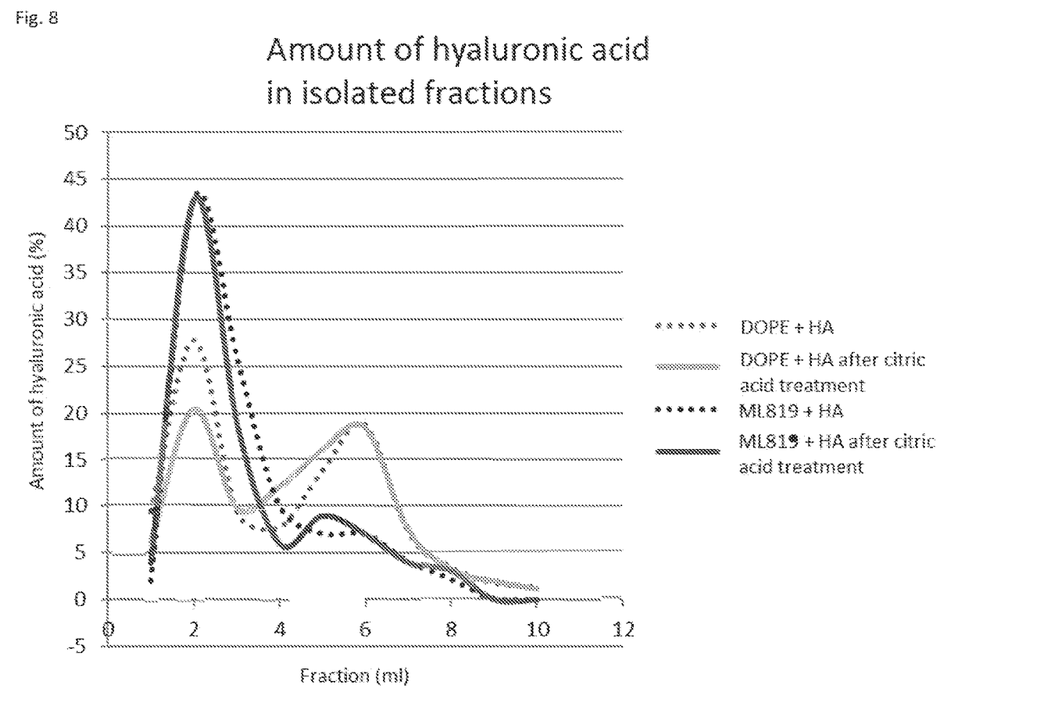
FIG. 8: Amounts of hyaluronic acid in individual fractions after separation by gel chromatography; fluorimetric detection.

Results: In the fraction containing liposomes (2 ml) in liposomes with aminooxylipid of general formula I (according to Example 14), 45% of the original HA amount was bound and did not change due to acidification. For the other aminooxylipids of general formula I (according to Example 12,13) the data was almost identical. For liposomes containing DOPE, 27% of the original HA was bound and 20% remained bound after acidification (FIG. 8).

Example 23

Binding of Liposomes Containing Aminooxylipids of General Formula I (According to Example 14) to H1299 Cells
Methods: Liposomes prepared as in Example 15, containing 0.4% fluorescent lipid in a volume of up to 10% of the total volume in a well were added to H1299 cells. The total amount of liposomes was 100 µg lipid per 1 ml medium. The level of cellular uptake of liposomes was measured on a flow cytometer FACSCalibur (Becton Dickinson, USA) and a fluorescence microscope (Nikon, Japan) was used for their observation.

Figure 9:
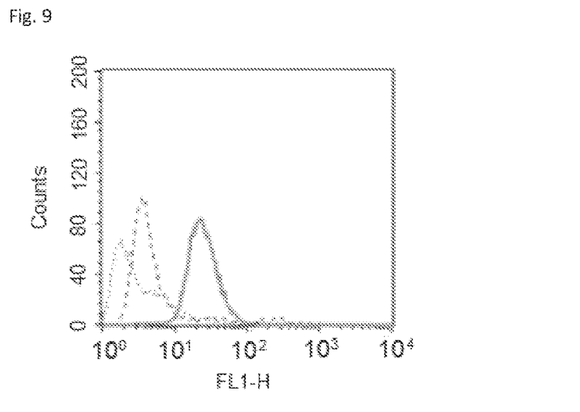
FIG. 9: Comparison of flow cytometry signals: cells alone (dotted line), cells after the addition of empty liposomes (dashed line), fluorescence of cells treated with hyaluronic acid-coated liposomes (solid line).
Figure 10:
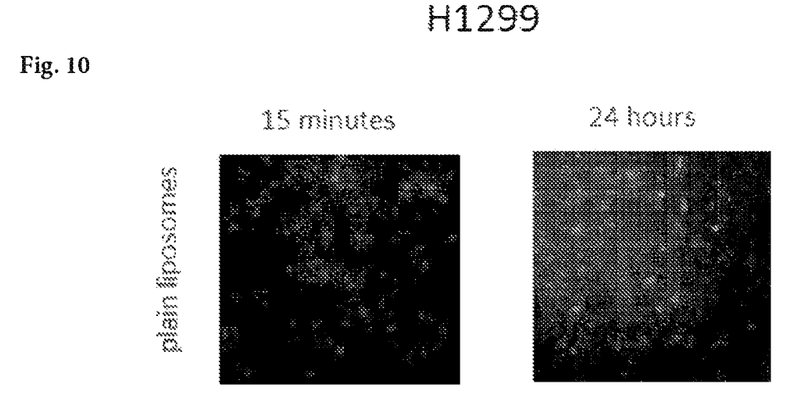
FIG. 10: Comparison of binding of empty vs. modified liposomes to H1299 surface after 15 minutes and 24 hours.

Results: Flow cytometry results (FIG. 9) and fluorescence microscopy results (FIG. 10) show that hyaluronic acid coating improves the binding of liposomes to cells via CD44 receptor. Liposomes coated with hyaluronic acid via the aminooxylipid can be used for targeting the cells expressing the CD44 receptor.

LITERATURE

Aberle, A. M.; Tablin, F.; Zhu, J.; Walker, N. J.; Gruenert, D. C.; Nantz, M. H., A novel tetraester construct that reduces cationic lipid-associated cytotoxicity. Implications for the onset of cytotoxicity. Biochemistry 1998, 37 (18), 6533-6540.

Baskin, J. M.; Prescher, J. A.; Laughlin, S. T.; Agard, N. J.; Chang, P. V.; Miller, I. A.; Lo, A.; Codelli, J. A.; Bertozzi, C. R., Copper-free click chemistry for dynamic in vivo imaging. *Proceedings of the National Academy of Sciences of the U.S. Pat. No.* 2,007,104 (43), 16793-16797.

Carmona, S.; Jorgensen, M. R.; Kolli, S.; Crowther, C.; Salazar, F. H.; Marion, P. L.; Fujino, M.; Natori, Y.; Thanou, M.; Arbuthnot, P.; Miller, A. D., Controlling HBV Replication in Vivo by Intravenous Administration of Triggered PEGylated siRNA-Nanoparticles. *Molecular Pharmaceutics* 2009, 6 (3), 706-717.

Drašar, L.; Ledvina, M.; Korvasova, Z.; Turanek, J., Lipopolyaminy sperminoveho typu pro konstrukci liposomálnich transfekčnich systémů. Czech. Pat. 303963, 2013.

Drašar, L.; Ledvina, M.; Korvasová, Z.; Turanek, J., Lipopolyamines of spermine type for construction of liposomal transfection systems. U.S. Pat. No. 9,393,200 B2, 2016.

Hassane, F. S.; Frisch, B.; Schuber, F., Targeted liposomes: Convenient coupling of ligands to preformed vesicles using "click chemistry". *Bioconjugate Chemistry* 2006, 17 (3), 849-854; (b) Heyes, J. A.; Niculescu-Duvaz, D.; Cooper, R. G.; Springer, C. J., Synthesis of novel cationic lipids: Effect of structural modification on the efficiency of gene transfer. *Journal of Medicinal Chemistry* 2002, 45 (1), 99-114.

Korvasova, Z.; Drasar, L.; Masek, J.; Knotigova, P. T.; Kulich, P.; Matiasovic, J.; Kovarcik, K.; Bartheldyova, E.; Koudelka, S.; Skrabalova, M.; Miller, A. D.; Holy, A.; Ledvina, M.; Turanek, J., Antiviral effect of HPMPC (Cidofovir®), entrapped in cationic liposomes: In vitro study on MDBK cell and BHV-1 virus. *Journal of Controlled Release* 2012, 160 (2), 330-338.

Koudelka, S; Mikulik, R; Masek, J; Raska, M; Knotigova, P T; Miller, A D; Turanek, J. Liposomal nanocarriers for plasminogen activators. *Journal of Controlled Release* 2016, 22, 45-577.

Kusumoto, S.; Inage, M.; Shiba, T.; Azuma, I.; Yamamura, Y., Synthesis of long-chain fatty-acid esters of normal-acetylmuramyl-l-alanyl-d-isoglutamine in relation to antitumor activity. *Tetrahedron Letters* 1978, (49), 4899-4902.

Leventis, R.; Silvius, J. R., Interactions of mammalian-cells with lipid dispersions containing novel metabolizable cationic amphiphiles. *Biochimica Et Biophysica Acta* 1990, 1023 (1), 124-132.

Liu, Y.; Feizi, T.; Carnpanero-Rhodes, M. A.; Childs, R. A.; Zhang, Y. N.; Muiioy, B.; Evans, P. G.; Osborn, H. M. I.; Otto, D.; Crocker, P. R.; Chai, W. C., Neoglycolipid probes prepared via oxime ligation for microarray analysis of oligosaccharide-protein interactions. *Chemistry & Biology* 2007, 14 (7), 847-859.

Lv, H.; Zhang, S.; Wang, B.; Cui, S.; Yan, J., Toxicity of cationic lipids and cationic polymers in gene delivery. *Journal of Controlled Release* 2006, 114 (1), 100-109.

Marques-Gallego, P.; de Kroon, A., Ligation Strategies for Targeting Liposomal Nanocarriers. *Biomed Research International* 2014, 2014, 1-12.

Miller, A. D.; Keler, M.; Jorgensen, M.; Perouzel, E. US patent application publication, Pub. No. US 2005/0287202 A1.

Niculescu-Duvaz, D.; Heyes, J.; Springer, C. J., Structure-activity relationship in cationic lipid mediated gene transfection. *Current Medicinal Chemistry* 2003, 10 (14), 1233-1261.

Tang, L.; Yin, Q.; Xu, Y.; Zhou, Q.; Cai, K.; Yen, J.; Dobrucki, L. W.; Cheng, J., Bioorthogonal Oxime Ligation Mediated Cancer Targeting. *Chem Sci* 2015, 6 (4), 2182-2186.

Turánek, J.; Mašek, J.; Raška, M.; Ledvina, M., Application of Liposomes for Construction of Vaccines. In *Biomedical Science, Engineering and Technology*, Ghista, D. N., Ed. InTech, January, 2012: 2012; pp 653-678.

Ulrich, S.; Boturyn, D.; Marra, A.; Renaudet, O.; Dumy, P., Oxime Ligation: A Chemoselective Click-Type Reaction for Accessing Multifunctional Biomolecular Constructs. *Chemistry—a European Journal* 2014, 20 (1), 34-41.

Vabbilisetty, P.; Sun, X. L., Liposome surface functionalization based on different anchoring lipids via Staudinger ligation. *Organic & Biomolecular Chemistry* 2014, 12 (8), 1237-1244.

The invention claimed is:

1. Aminooxylipids of general formula I wherein $n_1$=5-30 and X is polymethylene linker of the general formula II wherein $n_2$=2-10, or X is polyethylene glycol linker of the general formula III wherein $n_3$=1-14.

2. Aminooxylipids of general formula I according to claim 1 characterized in that $n_1$=13 and X is polymethylene linker of the general formula II defined in the claim 1, wherein $n_2$=2 or 3, or X is polyethylene glycol linker of the general formula III defined in the claim 1, wherein $n_3$=1.

* * * * *